(12) United States Patent
Rikiishi et al.

(10) Patent No.: US 6,291,244 B1
(45) Date of Patent: Sep. 18, 2001

(54) METHOD OF PRODUCING TRANSFORMED CELLS OF BARLEY

(75) Inventors: Kazuhide Rikiishi; Kazuhiko Noda, both of Kurashiki; Makoto Kihara, Gunma-ken, all of (JP)

(73) Assignee: Sapporo Breweries Limited, Tokyo (JP)

( * ) Notice: Subject to any disclaimer, the term of this patent is extended or adjusted under 35 U.S.C. 154(b) by 0 days.

(21) Appl. No.: 09/462,499

(22) PCT Filed: Jul. 6, 1998

(86) PCT No.: PCT/JP98/03026

§ 371 Date: Jan. 24, 2000

§ 102(e) Date: Jan. 24, 2000

(87) PCT Pub. No.: WO99/04618

PCT Pub. Date: Feb. 4, 1999

(30) Foreign Application Priority Data

Jul. 25, 1997 (JP) .................................................. 9-213938

(51) Int. Cl.$^7$ ............................ C12N 15/82; C12N 15/87
(52) U.S. Cl. ......................... 435/469; 435/468; 800/278; 800/294

(58) Field of Search .............................. 435/173.5, 172.3, 435/113, 415, 426, 430, 419, 469, 69.1, 430.1, 320.1

(56) References Cited

U.S. PATENT DOCUMENTS

| 5,244,794 | * | 9/1993 | Prince et al. | .......................... | 435/113 |
| 5,591,616 | * | 1/1997 | Hiei et al. | .......................... | 435/172.3 |
| 5,693,512 | * | 12/1997 | Finer et al. | .......................... | 435/173.5 |

* cited by examiner

*Primary Examiner*—Amy J. Nelson
*Assistant Examiner*—David H Kruse
(74) *Attorney, Agent, or Firm*—Oblon, Spivak, McClelland, Maier & Neustadt, P.C.

(57) ABSTRACT

The present invention relates to a method of producing transformed cells of barley by suspending, in a suspension medium containing 200–1000 mg/l acetosyringone, a microorganism belonging to the genus Agrobacterium containing a foreign gene; and culturing, in a co-culture medium containing about 1000 mg/l acetosyringone, the microorganism belonging to the genus Agrobacterium and barley callus cells; separating the cultured barley cells from the co-culture medium; and placing the separated barley cells on a selective medium to select the transformed cells into which the foreign gene has been introduced.

2 Claims, No Drawings

METHOD OF PRODUCING TRANSFORMED CELLS OF BARLEY

FIELD OF THE INVENTION

The present invention relates to a method for transformation of barley cells.

DESCRIPTION OF THE RELATED ART

Known major methods of producing transformed plants such as barley (Hordeum) from the Gramineae family include a method of direct gene transfer into protoplasts (Funatsuki et al., 1995, Theor. Appl. Genet.,91:707–712) and a method using a particle gun (Wan and Lemaux, 1994, Plant Physiol., 104:37–48).

In the protoplast method, however, there remain many aspects to be improved with respect to the efficiency of production of transformed plants, applicable varieties etc. On the other hand, in the particle gun method there remain many aspects to be improved with respect to necessity for a special device as well as applicable varieties etc., like the protoplast method.

Recently, it has been revealed that a transformation method using microorganisms belonging to the genus Agrobacterium is effective in transformation of cereals such as rice (Chan et al.. 1993, Plant Mol. Biol.,22:491–506; Hiei et al., 1994, Plant J., 6: 271–282).

This method using the Agrobacterium does not require any technique for plant regeneration from protoplasts or any special device such as particle gun and is thus considered to be a very effective transformation method. For barley, however, production of transgenic plants with microorganisms belonging to the genus Agrobacterium is only one example (Tingay et al., 1997, Plant J., 11:1369–1376), and establishment of a transformation system for barley by microorganisms belonging to the genus Agrobacterium is desired.

EP 0 604 662A mentions a method of transforming monocotyledon. Godwin, I. et al. (1991), Plant Cell Reports 9, 671–675 discloses that the effects of acetosyringone and pH on Agrobacterium-mediated transformation vary according to plant species. Further, Aldemita, R. R. (1996), Planta, 199, 612–617 mentions the genetic transformation of rice mediated by *Agrobacterium tumefaciens*.

SUMMARY OF THE INVENTION

An object of the present invention is to provide a method of efficiently transforming barley cells by improving the above-mentioned method of producing transgenic plants by use of microorganisms belonging to the genus Agrobacterium which was utilised in transformation of rice plants (Chan et al., 1993, Plant Mol. Biol., 022:491–506; Hiei et al., 1994, Plant J., 6:271–282).

As a result of their eager study under these circumstances, the present inventors found that in the case where barley cells are transformed with a microorganism belonging to the genus Agrobacterium, barley cells can be transformed efficiently by co-culturing the barley cells with a microorganism belonging to the genus Agrobacterium in the presence of acetosyringone at a significantly higher concentration than in transformation of rice plants and for a longer period of time under lower temperature conditions than usual, and the present inventors thereby arrived at the present invention.

The first aspect of the present invention is a method of producing transformed cells of barley, comprising the steps consisting of:
1) suspending, in a suspension medium, a microorganism belonging to the genus Agrobacterium having a transformation ability with a foreign gene and containing said foreign gene;
2) culturing, in a co-culture medium, the microorganism belonging to the genus Agrobacterium suspended in said suspension medium and barley cells with calluses induced on a callus induction medium;
3) separating the cultured barley cells from the co-culture medium; and
4) placing the separated barley cells on a selective medium to select the transformed cells into which the gene has been introduced.

The second aspect of the present invention is a production method according to claim 1 wherein the suspension medium contains 200 to 1000 mg/l acetosyringone.

The third aspect of the present invention is a production method according to the above method 1 or 2 wherein the co-culture medium contains 200 to 1000 mg/l acetosyringone.

The fourth aspect of the present invention is a production method according to any one of the above methods 1 to 3 wherein the culture in the co-culture medium is carried out at 20 to 24° C. for 5 to 7 days.

DETAILED DESCRIPTION OF THE PREFERRED EMBODIMENTS

Hereinafter, the present invention is described by reference to preferred embodiments.

First, calluses with a high differentiation ability are induced from barley tissues. Although the material used here is not particularly limited, immature embryos of barley 8 to 20 days after pollination are preferably used.

As the callus induction medium, use is made of an agar medium containing auxins such as IAA (indole acetic acid), 2,4-D (2,4-dichlorophenoxy acetic acid), picrolam, dicanba etc. Induction of calluses is carried out by culturing immature embryos of barley at 20 to 30° C. for about 3 days after placed on said medium.

Although the strain of the microorganism belonging to the genus Agrobacterium is not particularly limited, a strain carrying a reporter gene such as GUS gene or the like is preferably used to confirm expression of a gene introduced into cells. A typical strain is *Agrobacterium tumefaciens*.

Suspension cells of this microorganism belonging to the genus Agrobacterium are then prepared. The microorganism belonging to the genus Agrobacterium cultured on the agar medium is transferred to and suspended in an acetosyringone-containing liquid medium (referred to hereinafter as suspension medium).

A gene can be introduced into barley cells more efficiently at a higher concentration of acetosyringone in the suspension medium where a concentration of 200 to 1000 mg/L is suitably used for the present invention.

The microorganism belonging to the genus Agrobacterium and barley cells with calluses induced on the callus induction medium, both suspended in the suspension medium, are co-cultured. That is, barley cells are immersed in the suspension medium at a regulated concentration and then co-cultured on said agar medium containing acetosyringone.

As a result of examination of the concentration of acetosyringone in the co-culture medium, it was found that a particularly higher concentration than the usual concentration (10 mg/L) used for plants such as rice is preferable in the case of barley, and introduction of a foreign gene into barley cells is particularly effective where acetosyringone is used at a concentration of 200 to 1000 mg/L.

With respect to other conditions for co-culture, the period of culture is preferably a longer period such as 5 to 7 days. The period of co-culture of barley cells in conventional methods ranges from 2 to 3 days, but introduction of a foreign gene into the barley cells is inadequate. The culture temperature is preferably a lower temperature than the conventional temperature range of 25 to 28° C. used for plants such as rice, so that growth of the microorganism belonging to the genus Agrobacterium can be inhibited and the period of co-culture can be prolonged, and the temperature range of 20 to 24 ° C. is found to be preferable for introduction of a foreign gene into barley cells.

Then, the barley cells thus co-cultured with the microorganism belonging to the genus Agrobacterium is washed with carbenicillin, cephotatis etc. and then placed on a selective medium containing antibiotics such as kanamycin, hygromycin etc. to permit selection of barley cells having the gene introduced into them.

While the transformed barley cells are selected, transient assays are conducted to confirm introduction of the gene into the cells. The method of such transient assays is varied depending on the type of the gene introduced, and in the case where the GUS gene is introduced, expression of the introduced gene can be easily confirmed by the GUS assay (Jefferson et al., 1987, EMBO J., 6: 3901–3907).

According to the present invention, barley cells can be transformed efficiently with a microorganism belonging to the genus Agrobacterium. Once regenerated plants are obtained from the resulting transformed cells, it is also possible to produce transformed barley. The transformation method of the present invention does not require any technique of plant regeneration from protoplasts or any special device such as particle gun, and is thus a very practical method.

EXAMPLES

Hereinafter, the present invention is described in more detail by reference to Examples which however are not intended to limit the scope of the present invention.

Example 1

Immature embryos (10 days after pollination) from the barley variety Lenins grown in a field was placed in an MSm2D solid medium prepared by adding 30 g/L maltose, 2 mg/L 2,4-D and 2 g/L Gel Light to an MSm medium (Jaehna et al., 1991, Theor. Appl. Genet., 82:74–80), and calluses were induced (pre-cultured) therefrom in a bright place at 25° C. for 3 days.

Separately, an EHAIOI (pIG121Hm) strain i.e. one strain of *Agrobacterium tumefaciens* was used as the microorganism belonging to the genus Agrobacterium. The EHA101 strain is described in Hood, E. E., G. L. Helmer, R. T. Fraley, M. D. Chilton, 1986, J. Bacteriol., 1291–1301, and plasmid pIG121Hm is described in Ohta, S., S. Mita, T. Hattori, K. Nakamura, 1990, Plant Cell Physiol., 31:805–813. This plasmid pIG121Hm is a kanamycin- and hygromycin-resistant vector containing the GUS gene.

The above strain from a glycerol stock was plated on a solid medium containing 50 mg/L kanamycin and 50 mg/L hygromycin and incubated in the dark at 28° C. for 3 days. This was scratched off with a sterilized spatula and suspended in the MSm2D liquid medium (referred to hereinafter as suspension medium) prepared by adding 30 g/L maltose, 2 mg/L 2,4-D and a predetermined amount of acetosyringone to the MSm medium. The density of the microorganism was adjusted to 0.15–0.2 in terms of OD 600 nm.

Shoots and roots were removed from the immature embryos pre-cultured for 3 days, and then immersed for 90 seconds in the suspension medium. Excess water was removed therefrom with a sterilized paper towel, and the embryos were placed in the above MSm2D co-culture medium containing 10 g/L glucose and a predetermined amount of acetosyringone, and co-cultured for 3 days. The immature embryos thus co-cultured were washed sufficiently with solution containing 500 mg/L carbenicillin. Thereafter, excess water was removed therefrom with a sterilized paper towel and placed on the MSm2D selection medium containing 50 mg/L hygromycin and 500 mg/L carbenicillin.

3 days later, introduction of the GUS gene into barley cells and its expression were examined in a transient test using GUS assays.

The results are shown in Table 1.

TABLE 1

Effect of acetosyringone concentration in GUS assays

Acetosyringone concentration (mg/L)

| in the suspension medium | in the co-culture medium | A | B (%$^c$) | D |
|---|---|---|---|---|
| 10 | 10 | 98 | 8 (8.2) | 3.1 |
|  | 200 | 84 | 3 (3.6) | 2.3 |
|  | 1000 | 43 | 0 (0.0) | — |
| 200 | 10 | 112 | 3 (2.7) | 2.0 |
|  | 200 | 114 | 3 (2.6) | 4.3 |
|  | 1000 | 114 | 4 (3.5) | 40.8 |
| 1000 | 10 | 70 | 2 (2.9) | 4.0 |
|  | 200 | 52 | 6 (11.5) | 9.5 |
|  | 1000 | 27 | 3 (11.1) | 32.7 |

A: The number of immature embryos placed in the co-culture medium.
B: The number of immature embryos which showed blue spot formation, indicating expression level of the introduced gene.
C: (The number of immature embryos which showed blue spot formation/the number of immature embryos placed in the co-culture medium) × 100
D: The mean number of blue spots formed in each immature embryo which showed blue spot formation.

As is evident from the table, the mean number of formed blue spots per immature embryo is higher where the concentration of acetosyringone in the suspension medium is higher, indicating effective introduction of the gene into barley cells. It was further revealed that the gene is introduced effectively into barley cells where the concentration of acetosyringone in the co-culture medium is 200 to 1000 mg/l.

Example 2

In this example, the culture period and temperature conditions in co-culture were examined in the same manner as in Example 1 except that the culture period used was 3 days or 6 days and co-culture was conducted at predetermined temperatures. Introduction of the GUS gene into barley cells and its expression were examined in the transient test using GUS assays. The results are shown in Tables 2 and 3.

TABLE 2

Effect of temperature and acetosyringone concentration for co-culture in GUS assays (period of co-culture: 3 days).

| Temperature (° C.) | Acetosyringone concentration (mg/L) | A | B(%$^c$) | D |
|---|---|---|---|---|
| 20 | 10 | 30 | 0 (0.0) | — |
|  | 200 | 29 | 2 (6.9) | 6.0 |
|  | 1000 | 29 | 0 (0.0) | — |
| 24 | 10 | 31 | 3 (9.7) | 3.3 |
|  | 200 | 27 | 3 (11.1) | 1.3 |
|  | 1000 | 30 | 3 (10.0) | 4.0 |
| 28 | 10 | 31 | 3 (9.7) | 9.0 |
|  | 200 | 30 | 3 (10.0) | 19.3 |
|  | 1000 | 30 | 1 (3.3) | 6.0 |

A: The number of immature embryos placed in the co-culture medium.
B: The number of immature embryos which showed blue spot formation, indicating expression level of the introduced gene.
C: (The number of immature embryos which showed blue spot formation/ the number of immature embryos placed in the co-culture medium) × 100
D: The mean number of blue spots formed in each immature embryo which showed blue spot formation.

TABLE 3

Effect of temperature and acetosyringone concentration for co-culture in GUS assays (period of co-culture: 6 days).

| Temperature (° C.) | Acetosyringone concentration (mg/L) | A | B(%$^c$) | D |
|---|---|---|---|---|
| 20 | 10 | 16 | 0 (0.0) | — |
|  | 200 | 15 | 4 (26.7) | 2.3 |
|  | 1000 | 15 | 2 (13.3) | 16.0 |
| 24 | 10 | 15 | 2 (13.3) | 8.5 |
|  | 200 | 14 | 3 (21.4) | 8.0 |
|  | 1000 | 15 | 1 (6.7) | 121.0 |

A: The number of immature embryos placed in the co-culture medium.
B: The number of immature embryos which showed blue spot formation, indicating expression level of the introduced gene.
C: (The number of immature embryos which showed blue spot formation/ the number of immature embryos placed in the co-culture medium) × 100
D: The mean number of blue spots formed in each immature embryo which showed blue spot formation.

As is evident from these tables, the effect of introducing the gene into barley cells is higher when the culture period is longer and the temperature is 20 to 24° C.

What is claimed is:

1. A method of producing transformed cells of barley, comprising:

(a) suspending, in a suspension medium containing 200 to 1000 mg/l acetosyringone, a microorganism belonging to the genus Agrobacterium comprising a foreign gene;

(b) culturing, in a co-culture medium containing about 1000 mg/l acetosyringone, the microorganism belonging to the genus Aprobacterum and barley callus cells;

(c) separating the cultured barley callus cells from the co-culture medium; and (d) placing the separated barley callus cells on a selective medium to select the transformed cells into which the foreign gene has been introduced.

2. The method according to claim 1 wherein the culturing in the co-culture medium is carried out at 20 to 24° C. for 5 to 7 days.

* * * * *